US00PP24363P3

(12) United States Plant Patent
Bourne

(10) Patent No.: US PP24,363 P3
(45) Date of Patent: Apr. 1, 2014

(54) ***DIANTHUS* PLANT NAMED 'WP10 SAB06'**

(50) Latin Name: *Dianthus×hybrida*
Varietal Denomination: WP10 SAB06

(76) Inventor: Carolyn Grace Bourne, Dawlish (GB)

( * ) Notice: Subject to any disclaimer, the term of this patent is extended or adjusted under 35 U.S.C. 154(b) by 360 days.

(21) Appl. No.: 13/134,119

(22) Filed: May 31, 2011

(65) Prior Publication Data

US 2011/0239340 P1 Sep. 29, 2011

Related U.S. Application Data

(60) Provisional application No. 61/398,971, filed on Jul. 2, 2010.

(51) Int. Cl.
*A01H 5/00* (2006.01)

(52) U.S. Cl.
USPC ..... Plt./272; Plt./283

(58) Field of Classification Search
USPC ..... Plt./272, 283, 281
See application file for complete search history.

*Primary Examiner* — June Hwu
*Assistant Examiner* — Louanne Krawczewicz Myers

(57) ABSTRACT

A new cultivar of *Dianthus* plant named 'WP10 SAB06' which is characterized by compact plant habit and fragrant double flowers which are vibrant orange-pink in color. In combination, these characteristics set 'WP10 SAB06' apart from all other existing varieties of *Dianthus* known to the inventor.

2 Drawing Sheets

Genus: *DIANTHUS.*
Species: ×*hybrida.*
Denomination: 'WP10 SAB06'.

BACKGROUND OF THE INVENTION

The present invention relates to a new and distinct cultivar of hardy *Dianthus,* also known as garden pink, which is grown for use as a flowering plant for pots and containers and for planting in the garden and landscape. The new cultivar is known botanically as *Dianthus×hybrida* and will be referred to hereinafter by the cultivar name 'WP10 SAB06'.

'WP10 SAB06' is a complex hybrid plant that is the product of a long term breeding program conducted by the inventor in a cultivated area of Houndspool, Dawlish, Devon, United Kingdom. The inventor selected 'WP10 SAB06' in 2006 for its fragrant flowers which are double and vibrant orange-pink in color.

'WP10 SAB06' resulted from the controlled pollination between two unreleased and unpatented selections of *Dianthus* from the inventor's breeding program, namely Selection 'Marcella' as male parent and Selection 'SCA 03.10' as female parent.

'WP10 SAB06' is distinguishable from the male parent as follows: The flowers of the male parent are double and orange-pink in color, whereas the flowers of 'WP10 SAB06' are double and vibrant orange-pink in color. 'WP10 SAB06' is distinguishable from the female parent as follows: The female plant has a spreading vegetative habit with thin leaves and produces semi-double flowers with smooth edged petals, whereas 'WP10 SAB06' has a compact habit and broader leaves and produces fully double flowers with crenellated edged petals.

The variety of *Dianthus* which is considered by the inventor to most closely resemble 'WP10 SAB06' is *Dianthus* 'WP08 ULR03' (U.S. Plant Pat. No. 21,396). 'WP08 ULR03' is similarly double. However, 'WP08 ULR03' has a less compact habit, the foliage is grey-green and the flowers are pink in color rather than the vibrant orange-pink color of 'WP10 SAB06'.

Asexual reproduction of 'WP10 SAB06' was first accomplished by the inventor in 2006 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP10 SAB06'. These traits in combination distinguish this cultivar from all other commercial varieties known to the inventor. 'WP10 SAB06' has not been tested under all possible conditions and phenotypic differences may be observed with variations in environmental, climatic and cultural conditions, however, without any variance in genotype.

1. *Dianthus* 'WP10 SAB06' exhibits a compact habit.
2. The flowers of *Dianthus* 'WP10 SAB06' are double.
3. The flowers of *Dianthus* 'WP10 SAB06' are vibrant orange-pink in color.
4. *Dianthus* 'WP10 SAB06' blooms from February through October.
5. *Dianthus* 'WP10 SAB06' exhibits grey-green foliage.
6. At nine months of age, the height of the foliage mound of *Dianthus* 'WP10 SAB06' is 15 cm to 20 cm, and the width is 10 cm to 13 cm.
7. *Dianthus* 'WP10 SAB06' is perennial and is hardy to −15° C.
8. *Dianthus* 'WP10 SAB06' is suitable for use as a flowering plant in pots and containers.

BRIEF DESCRIPTION OF THE DRAWINGS

The accompanying color drawings illustrate the overall appearance of the new *Dianthus* variety 'WP10 SAB06' showing colors as true as it is reasonably possible to obtain in colored reproductions of this type. Colors in the drawings may differ from the color values cited in the detailed botanical description, which accurately describe the actual colors of the new variety 'WP10 SAB06'.

Figure 1:
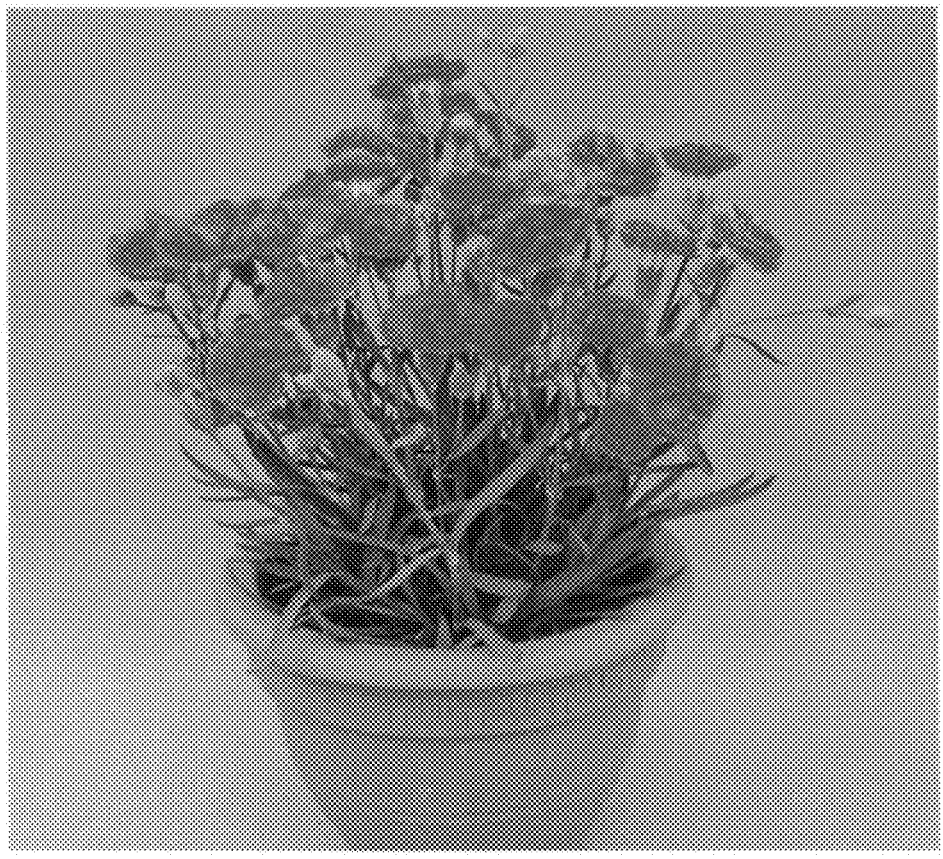

The drawing labeled as FIG. 1 depicts an entire flowering plant.

Figure 2:
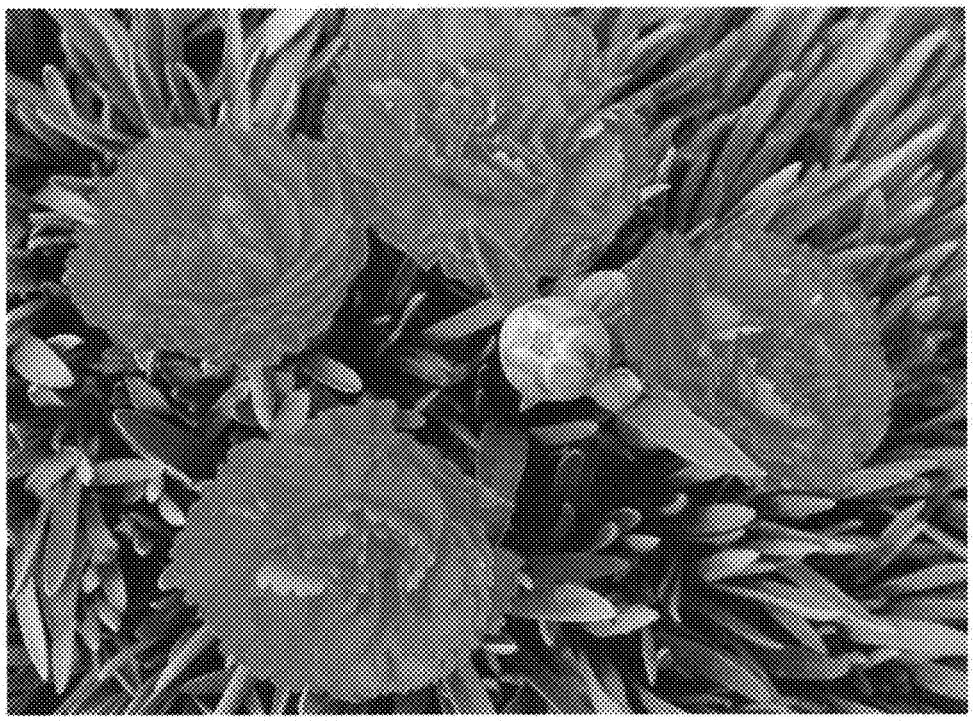

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP10 SAB06'. Data was collected in spring from 1.5-liter container plants in spring, and grown indoors in Devon, United Kingdom. The color determinations are in accordance with the 2001 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical: Classification:
- *Family*.—Caryophyllaceae.
- *Genus*.—*Dianthus*.
- *Species*.—×*hybrida*.

Denomination: 'WP10 SAB06'.

Parentage: A complex *Dianthus* hybrid whose immediate parents are unreleased hybrids from the inventor's breeding program, identified as follows:
- *Male parent*.—Unpatented selection of *Dianthus* from the inventor's breeding program, known as Selection 'Marcella'.
- *Female parent*.—Unpatented selection of *Dianthus* from the inventor's breeding program, known as Selection 'SCA 03.10'.

Plant type: Flowering perennial.

Use of plant: As a flowering plant in containers, window boxes, planters, pots and the garden.

Bloom period: February-October in Devon, UK.

Plant habit: A compact mound with many branches and stems upright.

Height of plant: 15 cm to 20 cm after 9 months.

Width of plant: 10 cm to 13 cm after 9 months.

Hardiness: Has survived in temperatures of minus 15 Centigrade, equivalent to USDA Hardiness Zone 7.

Root system: Many fibrous roots.

Propagation method: Vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 10-14 days are required to produce roots on a vegetative cutting.

Temperature for rooting: A minimum of 15° C. air temperature and 21° C. base temperature at root level is required to produce roots on the cuttings.

Facilities for rooting: Mist propagation unit is required for satisfactory rooting of cuttings.

Crop time (from planting a rooted cutting): 3 months starting in the Spring and 6 months starting in the Fall.

Plant stem:
- *Shape*.—Cylindrical.
- *Length*.—7 cm to 10 cm.
- *Diameter*.—3 mm in diameter.
- *Surface*.—Glabrous and glaucous.
- *Color*.—Ranges between N189A and N189B.
- *Branching*.—Numerous shoots from the axils of the lower leaves.
- *Internode length*.—From 1 mm (lowest internode) to 40 mm (uppermost internode).
- *Node dimensions*.—4 mm in diameter and 3 mm in length.

Leaf:
- *Type*.—Evergreen.
- *Shape*.—Linear.
- *Division*.—Simple.
- *Apex*.—Acute.
- *Base*.—Decurrent.
- *Venation*.—Faintly visible.
- *Margins*.—Entire.
- *Arrangement*.—Opposite and spiraling on stem.
- *Attachment*.—Sheathing.
- *Surface* (*adaxial and abaxial*).—Glaucous.
- *Stipules*.—Absent.
- *Fragrance*.—Absent.
- *Dimensions*.—Length: 5 cm to 8 cm. Width: 5 mm to 8 mm.
- *Color*.—Adaxial surface: N189B. Abaxial surface: 189A.

Inflorescence:
- *Flower stem*.—Length: 8-9 cm. Width: 3 mm. Stem strength: Erect. Stem color: Ranges between N189A and N189B.
- *Inflorescence*.—Cymose.
- *Type*.—Salviform, symmetrical.
- *Development*.—Singly, in sequence from the uppermost bud.

Buds:
- *Shape*.—Globular.
- *Dimensions*.—13 mm in length and 8 mm in width.
- *Color*.—139B and 143B.
- *Surface texture*.—Glabrous.

Flowers:
- *Number*.—3 to 5 per stem.
- *Pedicel dimensions*.—8 cm to 9 cm in length and 3 mm in width.
- *Pedicel strength*.—Erect.
- *Pedicel color*.—Ranges between N189A and N189B.
- *Flower dimensions*.—Length (including calyx): 35 to 40 mm. Diameter: 35 mm.
- *Flower shape*.—Circular.

Flower profile: Reflexed.
- *Lastingness*.—10 days at 20° C., on the plant.
- *Fragrance*.—Moderate to strong, spicy perfume.
- *Flowering period*.—February to October, in Devon, UK.

Corolla:
- *Shape* (*upper part of corolla*).—Flat Convex.
- *Shape* (*lower part of corolla*).—Concave.

*Petal arrangement.*—Persistent, apopetalous, overlapping.
*Petal margin.*—Crenate — dentate.
*Indentation.*—Varies between 0 mm and 2 mm.
*Petal texture.*—Soft.
*Flower type.*—Double.
*Petal number.*—30 to 35 true petals.
*Petal dimension.*—Length: 38 mm to 40 mm. Width: 20 mm to 22 mm.
*Color pattern.*—Blade is bright carmine, self color or single color.
*Color of upper surface.*—Ground color of blade: 46D and 52A. Color of band across blade: No band. Color of middle of strap: 145C. Color of base of strap: 145D.
*Color of lower surface.*—Ground color of blade: 47D. Color of middle of strap: 145C. Color of base of strap: 145D.
*Petal shape.*—Obdeltoid.
*Petal apex.*—Fan shaped.
*Petal base.*—Strap shaped, tapering towards base.
*Petal surface.*—Glabrous.

Calyx:
*Shape.*—Cylindrical.
*Sepal apex.*—Subacute.
*Sepal base.*—Fused.
*Longitudinal profile.*—Flat.
*Dimensions.*—Length: 20 mm. Diameter: 5-8 mm. Sepals: Fused to 5 mm below the apex.
*Sepals number.*—5.
*Sepals color, outer surface.*—Ranges between 137B and N138B towards sepal apex and between 144C and 144D towards sepal base.
*Sepals color, inner surface.*—144B to 144C.
*Anthocyanin.*—Absent.
*Splitting.*—Not observed.

Epicalyx:
*Bracts number.*—1 pair of two.
*Shape of outer lobe.*—Acuminate.
*Dimensions.*—Width: 7 mm to 8 mm. Length: 6 mm to 7 mm.
*Color.*—Predominantly N138A; 144C and 144D towards margin.
*Anthocyanin.*—Absent.

Bracteoles:
*Number.*—1 pair of two.
*Dimensions.*—Width: 10 mm. Length: 9 mm.
*Color.*—Predominantly N138A; 144C and 144D towards margin.
*Anthocyanin.*—Absent.

Reproductive organs:
*Stamens.*—Number: 10-15.
*Filaments.*—Number: 10 to 15. Color: White.
*Dimensions.*—Length: 20 mm in length and 0.5 mm in width.
*Anthers.*—Number: 10 to 15. Color: Cream to light pink. Length: 2 mm; diameter: 0.5 mm. Attachment: Dorsifixed.
*Pollen.*—Present.
*Pollen color.*—N155A.
*Style.*—Number: 2 to 4. Shoulder: Absent. Color: White. Length: 20 mm to 25 mm. Width: 0.5 mm.
*Stigma.*—Number: Single. Color: Light pink to light purple. Dimensions: 20 mm in length, 0.5 mm in width.
*Ovary.*—Position: Superior. Dimensions: Length: 8 mm to 10 mm. Diameter: 6 mm to 8 mm. Shape: Rhomboid. Color (upper surface): 145A. Color (lower surface): 145C.
*Seed.*—Seed has not been found during repeated observations.

The invention claimed is:

1. A new and distinct cultivar of *Dianthus* plant named 'WP10 SAB06' as described and illustrated herein.

* * * * *